(12) United States Patent
Laghi

(10) Patent No.: US 8,394,150 B2
(45) Date of Patent: *Mar. 12, 2013

(54) PROSTHETIC LINER WITH PROXIMAL SEAL

(75) Inventor: Aldo A. Laghi, Clearwater, FL (US)

(73) Assignee: ALPS Intellectual Property Management, LLC, St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/296,231

(22) Filed: Nov. 15, 2011

(65) Prior Publication Data

US 2012/0109336 A1    May 3, 2012

Related U.S. Application Data

(63) Continuation-in-part of application No. 12/381,146, filed on Mar. 6, 2009, now Pat. No. 8,357,206.

(51) Int. Cl.
*A61F 2/80* (2006.01)
(52) U.S. Cl. .......................................... 623/32; 623/34
(58) Field of Classification Search ............... 623/32–38
See application file for complete search history.

(56) References Cited

U.S. PATENT DOCUMENTS

| | | | |
|---|---|---|---|
| 2,696,011 A | 12/1953 | Galdik | |
| 5,314,497 A | 5/1994 | Fay et al. | |
| 5,728,170 A | 3/1998 | Becker et al. | |
| 5,830,237 A | 11/1998 | Kania | |
| 6,544,292 B1 | 4/2003 | Laghi | |
| 6,926,742 B2 | 8/2005 | Caspers et al. | |
| 7,427,298 B1 | 9/2008 | Swanson, Sr. | |
| 2004/0260403 A1 | 12/2004 | Patterson et al. | |
| 2009/0306791 A1 | 12/2009 | Slemker et al. | |
| 2011/0022183 A1 | 1/2011 | Slemker et al. | |

*Primary Examiner* — David Isabella
*Assistant Examiner* — Marcia Hoffman
(74) *Attorney, Agent, or Firm* — Shumaker, Loop & Kendrick, LLP; Henry J. Recla

(57) ABSTRACT

A prosthesis suspension assembly comprising: a prosthetic socket having an open proximal end and a closed distal end and an interior surface complementarily configured to a residual limb of an amputee, an interface or liner for receiving the residual limb and fittingly received in the socket, a distal outer surface of the liner comprises a porous or continuously cavitated, compressible material such as fabric and a proximal outer surface comprising an elastomeric material, a suspension sleeve which seals against the proximal outer surface of the liner and a proximal outer surface of the socket, and a locking pin connected to a distal end of the liner and lockingly retained in a hole in the distal end of the socket and including an air passage therethrough with a one-way valve therein for permitting the exit of air from an interstitial volume occupied buy said compressible material to atmosphere upon ambulation.

16 Claims, 6 Drawing Sheets

PROSTHETIC LINER WITH PROXIMAL SEAL

PRIORITY

This application is a Continuation-in-Part Application of U.S. application Ser. No. 12/381,146 filed on Mar. 6, 2009, which claims priority to U.S. provisional application Ser. No. 61/034,323, filed on Mar. 6, 2008.

BACKGROUND OF THE INVENTION

During the 1980's, a means of suspending a prosthesis was developed which consisted of a docking means fabricated into an interface which, in turn, was rolled onto the distal portion of the wearer's residual limb. The docking means engaged into the prosthesis, and the prosthesis was thereby locked in position of attachment to the patient's limb.

Such a means of attachment became standard in the industry. However, it had drawbacks which ultimately led to its supplantation by other methods. One major drawback was the tendency of the residual limb to piston, or slip upwards and downwards in the interface upon ambulation. Over the years, it has been thought that pistoning occurred because only the distal portion of the limb was involved in the support of the prosthesis. The limited support resulted in a high degree of angular and torsional stress at the interface of the socket/liner and the residual limb. The pistoning, in combination with the sucking effect caused by the interface, caused the limb to change in volume with ambulation. As a result, the fit of the prosthesis changed with wear throughout the day. It was necessary for the wearer to make use of a thick prosthetic sock on the residual limb in an attempt to compensate for the limb's change in volume during use of the prosthesis and alleviate some of the discomfort which was experienced as a result of pistoning. However, the sock added an inconvenient bulk to the already awkward task of wearing a prosthesis, as well as creating sanitary issues due to the collection of sweat and dirt.

In the 1990's, suspension sleeves were used to create a seal between the residual limb and the prosthesis. As illustrated in FIGS. 1 and 2, this type of suspension sleeve (4) is an elastic or elastomeric tube which, when properly positioned, forms a seal which encompasses 1) the proximal lip of the prosthesis socket (3), 2) the entire portion of the interfacing layer/liner (5) external to the socket, and 3) a portion of the wearer's thigh just above the proximal end (2') of the interfacing layer/liner. The sleeve, employed in its sealing capacity, is illustrated in FIG. 2. The seal created by the elastomeric sleeve is able to support a modest vacuum. The vacuum is typically in the range of from greater than about 2 inches Hg to about 14 inches Hg. One-way valves embedded in the prosthesis socket or interfacing layer/liner or pumps are often used to establish and maintain the vacuum.

The sealed socket limb junction of these prior art prostheses largely eliminates the pistoning problem. Furthermore, such prior art prostheses included a layer of fabric or other porous or continuously cavitated compressible material such as, for example, a synthetic foam, which overlies the entire interface and occupies an area between the socket and the interface, and serves to "wick" the vacuum to the entire volume occupied thereby, yet it prevents the interface from coming into contact with the socket, effectively establishing a volume over which a vacuum can be sustained.

However, this method introduces new problems. The upper reaches of the seal extend onto the thigh of the wearer, essentially including the skin of the wearer in the partially evacuated volume. The skin directly under the sleeve chafes from the elastic motion of the sleeve as the residual limb compresses and decompresses with the ambulation cycle. Furthermore, bending at the knee causes the sleeve to bunch directly behind the knee and on the back of the leg above the knee, and stretch tightly in the analogous positions on the front of the residual limb. Such motion can cause blistering and subsequent infection and pain, even to the extent of requiring the wearer to forego the use of the prosthetic for periods of time. Nevertheless, the sealing of the partially evacuated volume by extending the sleeve to the wearer's thigh, and the inclusion of the wearer's skin as a bounding surface to the partially evacuated volume have persisted as part of the solution to the pistoning problems arising from earlier designs.

To overcome such problems, it has been found that when 1) the outer surface of only a distal portion of the interfacing layer/liner is covered with a porous or continuously cavitated compressible material, 2) the proximal portion of the interfacing layer/liner has a sealable, preferably elastomeric outer surface, and 3) the proximal portion of the sleeve extends to and seals against the proximal portion of the interfacing layer/liner; the pistoning is still greatly reduced, even though the seal does not extend up onto the thigh. One such prior art system is disclosed in U.S. Pat. No. 7,427,297 to Patterson et al. which is incorporated herein by reference. Although the Patterson et al. prosthesis includes sealing sleeve 46, the present invention is an improvement in the sealing structure on these types of prostheses.

SUMMARY OF THE INVENTION

A prosthetic liner system surmounting the foregoing problems associated with the thigh-sealing liner system, yet maintaining the effectiveness against pistoning demonstrated by the thigh-sealing liner system would represent an advance in the prosthetic liner industry.

In one embodiment, the present invention comprises a prosthetic liner comprised of an elastomeric layer having a distal closed end and a proximal open end. The liner has a proximal edge, an inner surface and an outer surface. The outer surface is comprised of a layer of compressible porous or continuously cavitated material ("material" layer) which may be fabric. The liner is adapted to fittingly receive a residual limb of an amputee wherein the inner surface of the elastomeric layer contacts the residual limb. The material layer overlays the outer surface of the elastomeric layer except for a continuous region of the outer surface extending adjacent the proximal open end. At the material leading edge, the outer surface transitions from fabric to a circumferentially continuous region of the elastomeric layer comprising a circumferentially continuous sealable surface.

In a preferred embodiment, the prosthetic assembly of the present invention comprises a monolithic prosthetic socket having an inner surface and an outer surface, a closed distal end, an open proximal end, a proximal edge and a proximal outer surface region surrounding said proximal end and wherein said inner surface is configured to be substantially complimentary to the shape of a residual limb of an amputee. The assembly includes a prosthetic liner having an inner surface and an outer surface, a closed distal end and an open proximal end and wherein the inner surface is adapted to conform to the shape of a residual limb which is fittingly retained therein when donned. The liner further includes a proximal outer surface region surrounding the proximal end extending from a proximal edge of the liner to an intermediate edge and a distal outer surface region extending from said intermediate edge to the distal end of the liner. The distal outer surface region of the liner being covered with a porous or continuously cavitated compressible material such as fabric, but not limited thereto. The proximal outer surface region and the compressible material defining a substantially continuous surface for the liner such that when the liner is mounted within the socket, the distal outer surface region covered with the compressible material is fittingly received in the socket to thereby define and sustain an interstitial area between the inner surface of said socket and the outer surface of the liner occupied by the compressible material. The liner, when mounted in said socket, having the intermediate edge disposed adjacent to and within the proximal edge of said socket, and the proximal outer surface region of the liner extending away from said proximal edge of the socket. The prosthetic assembly also includes a sealing open-ended sleeve having a first end and an opposite second end. The sealing sleeve being mounted in sealing engagement over the proximal outer surface region of said socket and the proximal outer surface region of said liner with the first end overlapping the proximal outer surface region of said socket and said second end overlapping and terminating within the proximal outer surface region of said liner. As the amputee ambulates, air trapped within the interstitial area occupied by the compressible material is forced to evacuate therefrom through the compressible material and through the interface between the sealing sleeve, the proximal outer surface region of said socket and the proximal outer surface region of said liner.

In the preferred embodiment of the prosthetic assembly of the present invention as described above, the liner, compressible material and sealing sleeve are comprised of materials selected such that a vacuum from above about 0 inches Hg to about 15 inches Hg is capable of being maintained in the interstitial area occupied by the compressible material upon ambulatory motion.

In another preferred embodiment, the prosthetic assembly of the present invention comprises a pin mounted to the distal end of the liner which engages a hole or cavity in the prosthesis socket. The pin comprises an outer configuration that engages with a locking mechanism for locking the prosthesis onto the residual limb. The pin further comprises an internal passageway with a one-way valve mounted therein. The internal passageway upstream of the one-way is in fluidic communication with the interstitial region occupied by the compressible material. The internal passageway downstream of the one-way valve is in fluidic communication with the surrounding atmosphere. Alternatively, the pin could be connected to a vacuum pumping system mounted externally of the prosthesis such as around a pylon of an artificial leg adapted to be connected to the distal end of the socket or could be fluidically connected to a pumping system mounted internally of the prosthesis such as within a cavity inside of a pylon. With any of the above arrangements, air within the volume of the interstitial region will be force to exit through the one-way valve either by amputee ambulation and/or suction created by the pumping system.

The present invention is effective over a range of liner lengths. By liner length, it is meant the distance from the distal tip of the liner to the proximal edge of the proximal open end. Liner lengths in the range of from about 8 inches to about 30 inches are preferred, with lengths in the range of from about 12 to 24 inches more preferred. In general, it is desirable that the liner have a length such that, when worn, it extends at least about 5 inches up onto the wearer's residual limb as measured from the residual limb's most distal point.

The present invention makes use of the fitting parameters which are standard in the art, and thus, a liner which would be correctly fitted for the current thigh-seal method is generally correctly fitted for the purposes of the present invention. However, liners which may be considered uncomfortably tight or snug for use with the current thigh-seal method can, in some cases, be used comfortably with the suspension system of the present invention.

The liner of the present invention comprises an inner surface and an outer surface. The inner surface faces the residual limb, and in the absence of other lining materials, contacts or interfaces with the surface of the residual limb. The inner surface is conveniently a layer of elastomeric material preferably of a type compatible with long periods of dynamic wearer contact. Such materials are known in the art and may include the following polymers, as well as gels which comprise them: polyurethanes; block copolymers such as styrene block copolymers, general non-limiting examples of which may include SEBS-, SEPS-, SEEPS-, SEEBS-, and other type styrene block copolymers. Further non-limiting examples of styrene block copolymers which may be useful in the liner of the present invention include so called "controlled distribution polymers," such as, for example, those disclosed in U.S. Pat. No. 7,226,484; United States Patent Application Publication No. 20070238835; and United States Patent Application Publication No. 20050008669. Other potentially useful polymers may include certain so-called "crystalline" polymers, such as, for example, polymers disclosed in U.S. Pat. Nos. 5,952,396; 6,420,475; 6,148,830 and 6,148,830. The above list is non-limiting, and in general, the list of acceptable polymers and gels includes those known in the art to be useful for the fabrication of prosthetic liners. By the term "gel," is meant a polymer which has, associated with it, through means known in the art such as absorption, mixing, or other, a plasticizer. Gels which do not have a tendency to delaminate from the material layer are preferred.

It should be noted that the benefits of the present invention may be obtained even if the material layer contains other components, such as other layers of flexible materials (even if not elastomeric) as long as the surface of the material layer against which the suspension sleeve seals, described infra, is capable of sustaining the required vacuum.

Another aspect of the present invention is that the distal portion of the liner is modified to have or is covered with a porous or continuously cavitated compressible material. The compressible material does not extend to the proximal edge of the liner meaning that all points of the leading edge of the porous or continuously cavitated compressible layer are at least 1 centimeter away from all points on the proximal edge of the liner, and in other embodiments, at least 3, 5, 8 and 12 centimeters from all points on the proximal edge of the liner. In additional embodiments, the leading edge of the porous or continuously cavitated compressible layer and the proximal edge of the liner each lie in spaced-apart non-parallel planes and still, in other embodiments, the planes are parallel to each other and perpendicular to the long axis of the liner.

In one embodiment, the compressible material comprises fabric that overlies a distal portion of the interface or elastomeric layer. In another embodiment, the compressible material is in the shape of a liner which slips over the distal end of the liner. In another embodiment, the compressible material is bonded to the elastomeric layer. Included within, but not limiting the meaning of "bonded" is fabric that is glued, molded, dipped, affixed, adhered, or otherwise immobilized upon the surface of the elastomeric layer. In yet another embodiment, the compressible material can be integral to the elastomeric layer. This can be accomplished when the connection between the layers is a result of melting or other processes such as chemical processes, or the elastomeric layer is superficially processed to create a compressible layer from the elastomeric layer itself, such as, for non-limiting example, chemically or thermally treating the upper surface of the elastomeric layer to cause the upper surface to form a foam.

The liner can be of a wide range of thicknesses. In preferred embodiments, the liner has a thickness in the range of from about 1 millimeter to 6 millimeters, or even thicker or thinner, with a more preferred thickness in the range of from about 2 to about 4 millimeters. In general, it is not necessary for the thickness of the liner to be uniform throughout in order to obtain the benefits of the present invention. The present invention can be used on liners having thickness profiles which are non-uniform or extraordinarily thick or thin, such as profiles reflecting a material layer having a strategic distribution of extra cushioning or support, such as may be required for therapeutic purposes. Furthermore, the interface layer can comprise additional layers of uniform or non-uniform thickness, such as may be utilized to support or cushion certain regions of the liner. In general, the term "liner" also includes elastomeric layers which, optionally, comprises multiple layers of elastomeric materials adhered together.

It is, however, strongly preferred that the face of the proximal portion of the interface intended to contact the inner surface of the intended suspension sleeve be of such a quality that a seal is formed between the liner and the suspension sleeve which can sustain a moderate vacuum in the range of from about 2 inches Hg to about 14 inches Hg for long enough to enable the wearer to experience the benefits of the invention for significant periods of time, such as, for example at least about 0.5 hrs, and more preferably, at least about 1, 2 or 3 hours.

In yet another embodiment the seal, when formed from an assembly comprising the liner, the prosthetic socket and the sleeve, as well as the distally connected pin having a one-way valve therein permitting the exit of gas trapped in the interstitial region occupied by the compressible material, can sustain a vacuum in the foregoing range for at least 10 or 20 minutes, and preferably for at least 30, 40, 50 or 60 minutes of ambulatory motion. It should be noted that because one-way valves may vary in efficiency, the ability of the assembly to meet the foregoing time standards is a property not of the seal itself, but of the seal/valve combination.

As noted above, the liner also comprises a porous or continuously cavitated compressible material or "material." By "porous" is meant a material comprising interconnected cavities which vent to the surface of the material through channels or other cavities. Fabrics, particularly those of sufficient heaviness, as well other types of usable materials, such as foams and sponges are generally porous. By "continuously cavitated" is meant a material whose volume comprises interconnected cavities which are continuous with the exterior of the material. Lattice-type structures (i.e., those having interconnected cavities of regular shape and size) qualify as "continuously cavitated."

The material creates a volume over which a vacuum can be maintained. Its compressibility, even if only slight or incompletely reversible, such as in the case of most fabrics, enables the material, upon seeking to expand its volume after compression, to aid in the creation of a vacuum in the space bounded by the liner, the suspension sleeve, and the prosthetic socket (the "interstitial volume"). Furthermore, upon ambulation, the compressibility of the material enables a larger proportion of the air in the interstitial volume to be evacuated, either through the one-way valve, as discussed infra, or through the interfaces between the sleeve and the prosthesis or the sleeve and the proximal portion of the liner. Preferably, the material is a layer of fabric with sufficient heaviness and compressibility that it can define a volume over which a moderate vacuum in the range of from about 2 inches Hg to about 14 inches Hg can be established upon ambulatory motion.

As indicated infra, the material is distributed over the distal portion of the interface, leaving a circumferentially continuous proximal portion free of material. In one embodiment, the entire proximal portion is characterized by a surface having the ability to seal with the inner surface of a selected suspension sleeve such that a moderate vacuum in the range of from about 2 to 14 inches Hg is maintained for at least 30 minutes of ambulatory activity, and more preferably for at least 60 minutes of ambulatory activity. In another embodiment, at least a circumferentially continuous subportion of the aforementioned portion is characterized by a surface having the foregoing qualities.

It should be noted that the quality of the foregoing seal has a dependence on the ability of the inner surface of the suspension sleeve to seal distally with the outer surface of the prosthetic socket at a circumferentially continuous region distal to the socket edge. The quality of the foregoing seal also depends on the ability of the suspension sleeve to seal proximally at a circumferentially continuous region proximal to the material leading edge. By "circumferentially continuous" is meant pertaining to an area which circumscribes. Thus, in general, the suspension sleeve must be long enough to simultaneously engage in both seals. Furthermore, the suspension sleeve must have the combination of physical dimensions such as unstretched and stretched circumferences and elastic dimensions such as elasticity, tensile strength, deformability, and the like to in order to create efficient seals. This is considered to be within the purview of the prior art. Furthermore, the efficiency of the seal depends on the quality of the contact between the suspension sleeve and the respective surfaces. In a preferred embodiment, the suspension sleeve comprises one material which forms a seal which can sustain a moderate vacuum in the range of from greater than 2 inches Hg to about 14 inches Hg. In other embodiments, the sleeve comprises a material differential from one end to the other end such that the overall efficiency of sealing the interstitial volume is improved over the sealing efficiency of the material compositions of the respective ends. In another embodiment, the sleeve comprises regions of two distinct materials which are joined together. In an additional embodiment, the region of joining comprises horizontal overlap of regions of the respective. By "horizontal" is meant parallel to the cylindrical axis. In yet another embodiment, an additional component is included to enhance the quality of the seal, and, optionally, is used to improve the efficiency of the seal. Such a component can be an adhesive which is mild and temporary such that it improves the vacuum-holding power of the seal, yet allows the sleeve to be removed, undamaged by the wearer. In some instances, it may be convenient to use a band or other circumferential securing mechanism to increase the efficiency of the seal. In other cases bio-sealants or other intermediate layers which contact the liner on one side and the suspension sleeve on the other may be used. The purview of the present invention is considered to encompass methods or additional measures for improving the vacuum-sustaining ability of the seal, even if the seal in the absence of the method or measure does not exhibit the ability to maintain a vacuum in the range of from 2-14 inches with ambulation, as long as the seal in the presence of the methods or measures does maintain such efficiency.

DETAILED DESCRIPTION OF THE INVENTION

Figure 1:
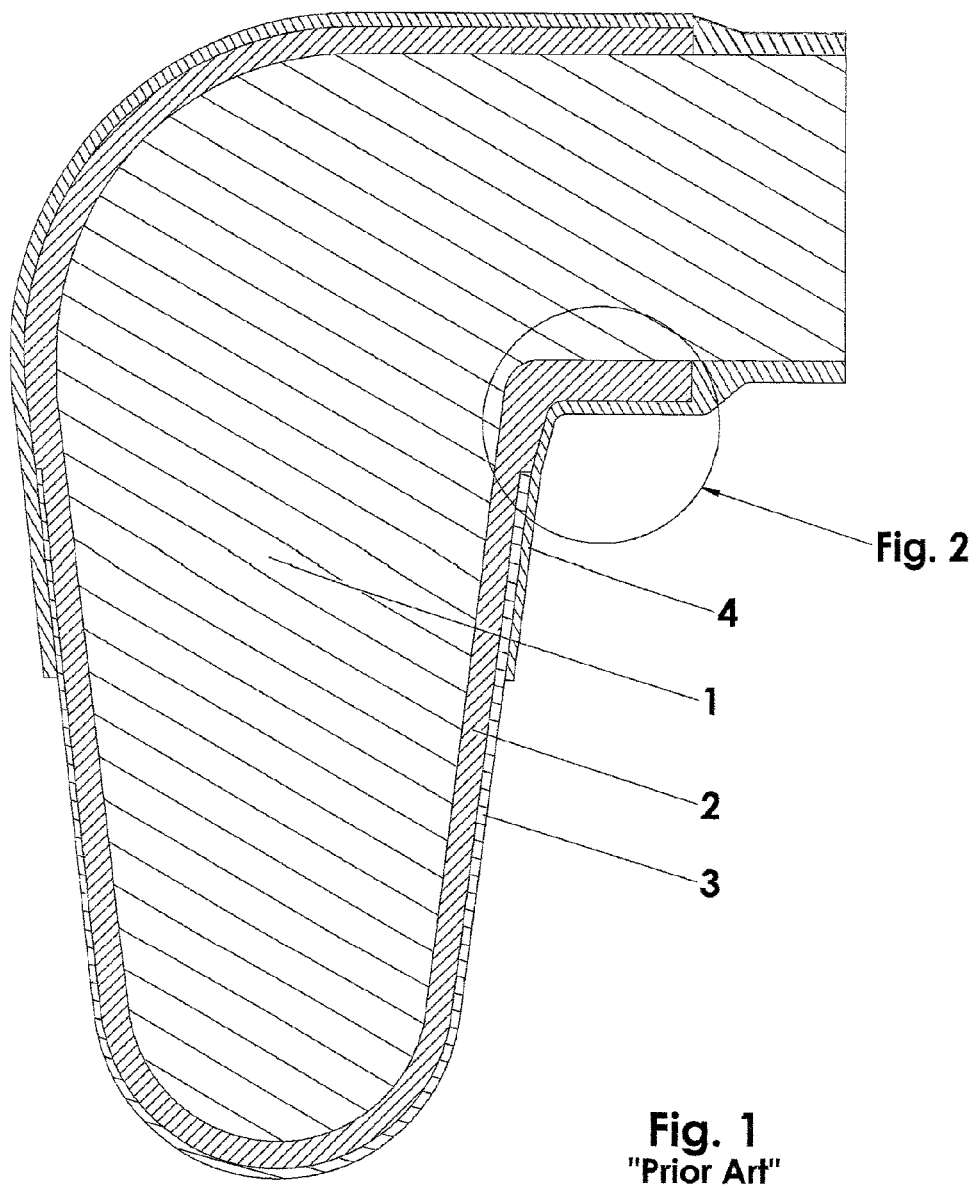
FIG. 1 is a cross-sectional view of a prior art prosthetic assembly illustrating the wearer's residual limb (1), a liner having a fabric layer (2), a prosthetic socket (3) and a suspension sleeve (4) acting as a sealing sleeve between the prosthetic socket and the residual limb.
Figure 2:
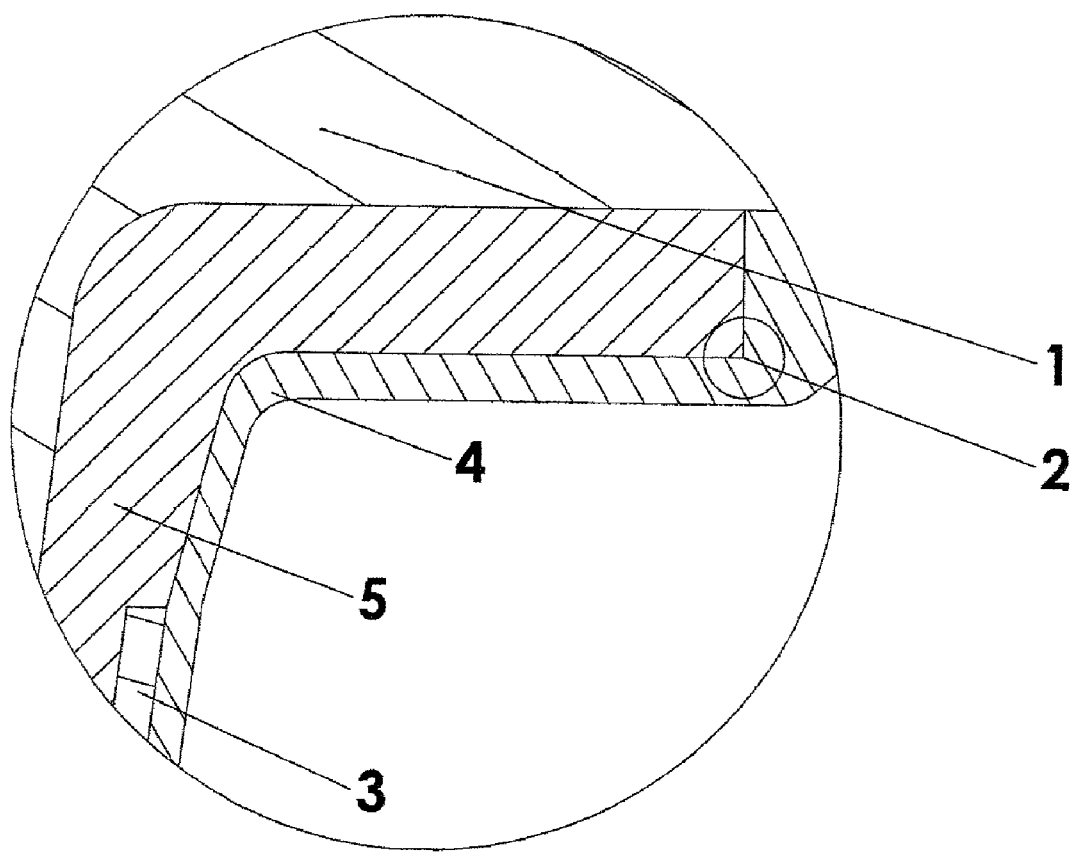
FIG. 2 is an enlarged cross-sectional view the suspension sleeve (4) as illustrated in FIG. 1.

FIGS. 1 and 2 illustrate a prior art prosthetic assembly. The liner includes a fabric layer (2) into which a wearer's prosthetic limb (1) is inserted. The limb/liner combination is inserted into a prosthetic socket (3). The prosthetic socket (3) has a proximal portion adjacent an intermediate portion (5) of fabric layer (2), against which the distal portion of a suspension sleeve (4) can seal, and which extends proximally, to some extent, up beyond the proximal end (2') of the fabric layer onto the residual limb (1). The suspension sleeve, in its proper functioning position, extends proximally from the socket, over the fabric liner, to the thigh of the patient, against which a seal is formed. A vacuum is established in the volume between the socket, the residual limb and the suspension sleeve.

Figure 3:
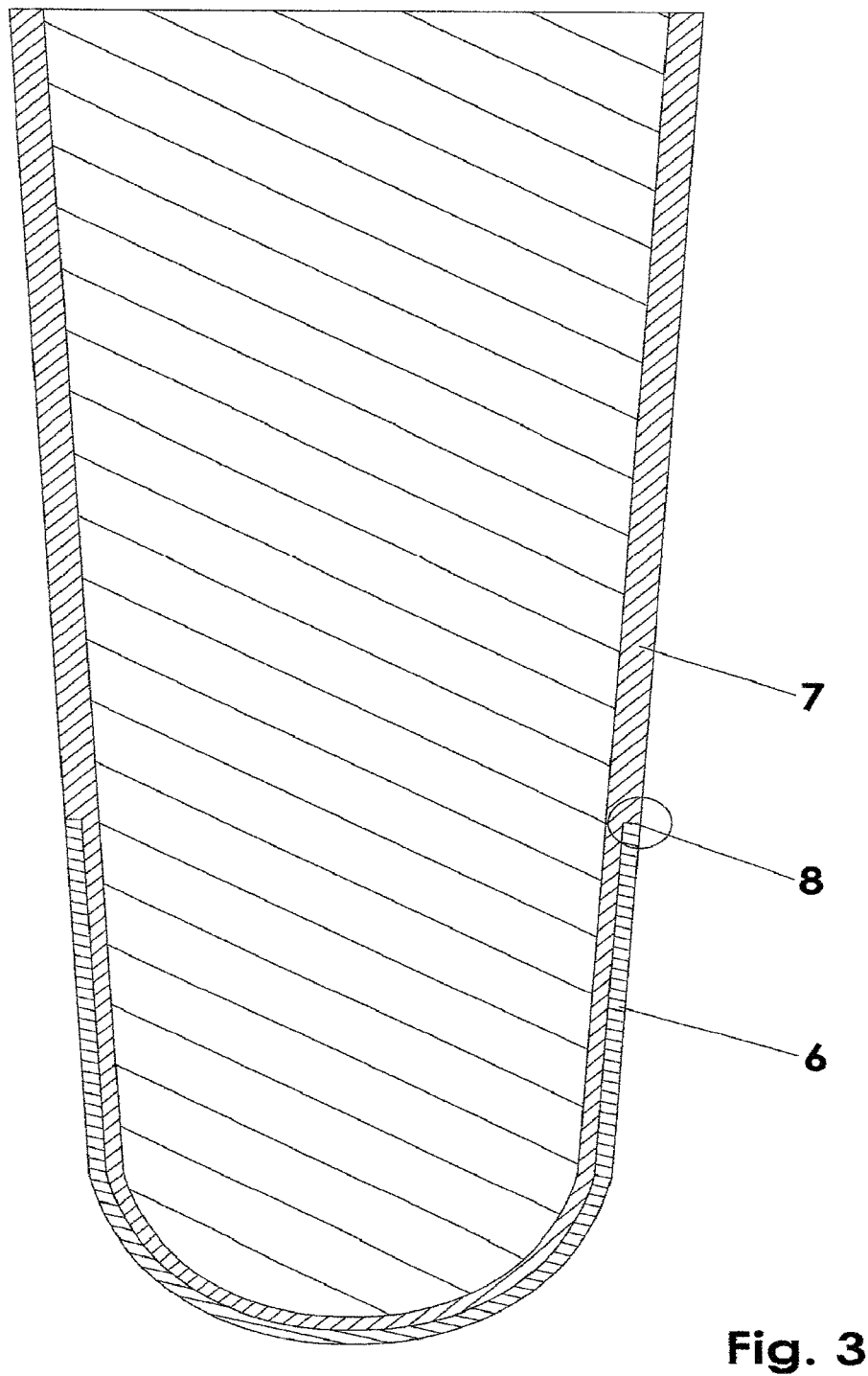
FIG. 3 is a cross-sectional view of a liner having an elastomeric layer (7) as well as a partial fabric outer layer (6).

FIG. 3 is an illustration of an embodiment of a liner of the present invention comprising an elastomeric layer or interface layer (7), and a material layer (6) which overlies the distal end of the elastomeric layer. The material layer comprises a leading edge (8). Shown is a fully recessed leading edge, in which the material layer is sunken into the surface of the interface or elastomeric layer.

Figure 4:
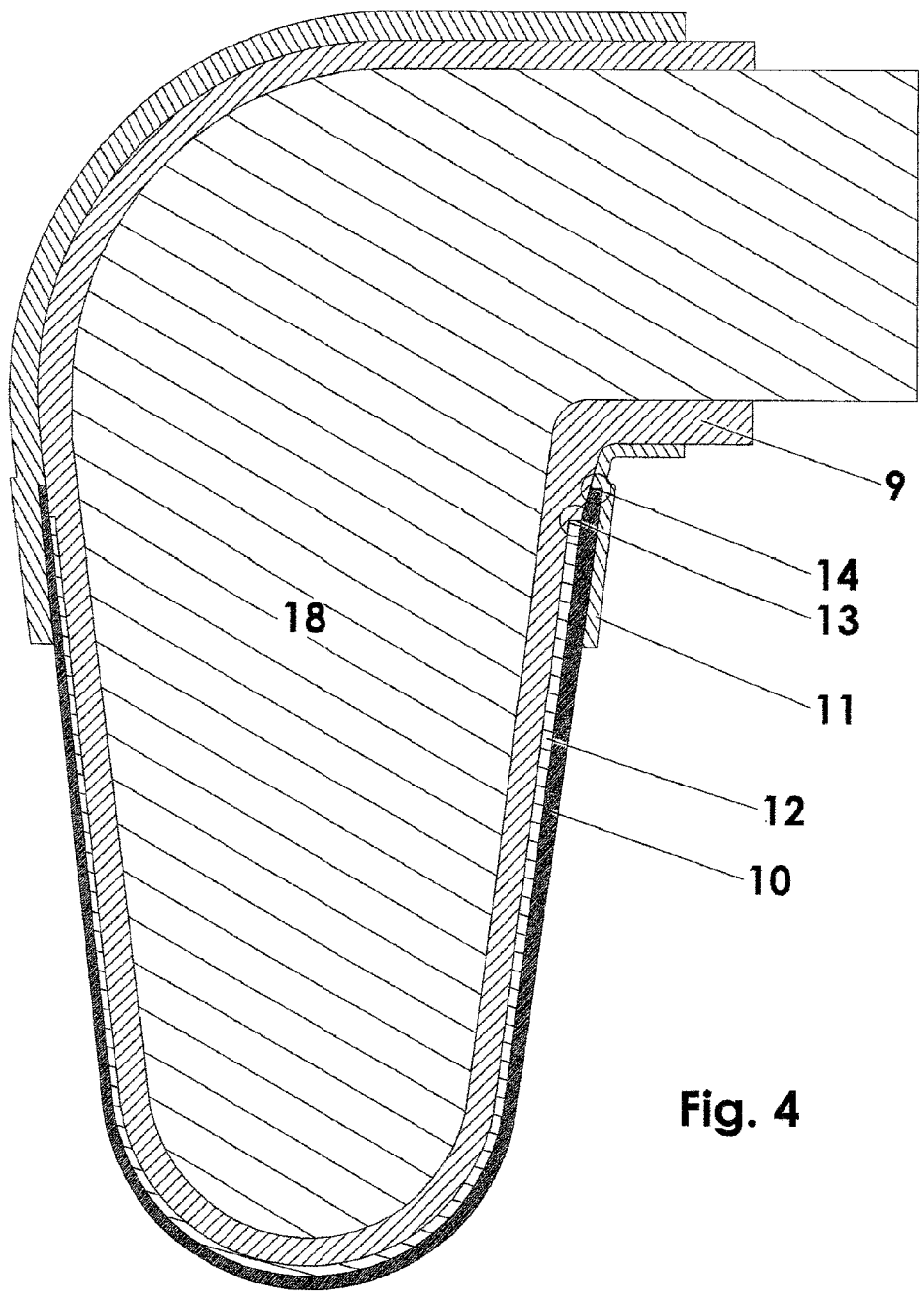
FIG. 4 is a cross-sectional view of a prosthetic assembly of the present invention showing the wearer's limb (18) within the elastomeric liner (9) having partial overlying material layer (12) mounted within prosthetic socket (10) and suspension sleeve (11).

FIG. 4 is an illustration of another embodiment of the present invention comprising a combination prosthetic socket/liner assembly. The prosthetic socket (10) is preferably a monolithic structure manufactured by any conventional technique to have an interior surface complementally configured to the residual limb of the amputee. The interface or elastomeric liner (9) has an open proximal end and a closed distal end for receiving a residual limb (18) fittingly retained therein. The outer surface of the elastomeric liner is distally overlaid with a material layer (12), which may be fabric, having a leading edge (13). The liner, when mounted in said socket, having the leading edge (13) act as an intermediate edge disposed adjacent to and within the proximal edge of said socket. The liner, when mounted in this position, having the proximal outer surface region of the liner between the intermediate edge of the liner and the proximal edge of the socket, sealing against the proximal inner surface of the socket and extending away from said proximal edge of the socket. The prosthetic assembly also includes a sealing open-ended sleeve (11) having a first end and an opposite second end. The sealing sleeve being mounted in sealing engagement over the proximal outer surface region of said socket and the proximal outer surface region of said liner with the first end overlapping the proximal outer surface region of said socket and said second end overlapping and terminating within the proximal outer surface region of said liner. If desired, an adhesive may be disposed on said proximal outer surface region of said socket and said proximal outer surface region of said liner, and which is mild and temporary such that it improves the vacuum-holding power of the seal between said sealing sleeve, socket and liner yet allows the sleeve to be removed, undamaged by the wearer.

Thus, with the above sealing arrangement, as the amputee ambulates, air trapped within the interstitial area occupied by the compressible material is forced to evacuate therefrom through the compressible material and then through the interface between the proximal outer surface region of the liner and the proximal inner surface region of the socket, through the interface between the proximal outer surface region of said socket and the sealing sleeve first end overlapping the proximal outer surface region of said socket, and through the interface between the proximal outer surface region of said liner and the sealing sleeve second end overlapping and terminating within the proximal outer surface region of said liner.

Figures 5, 6:
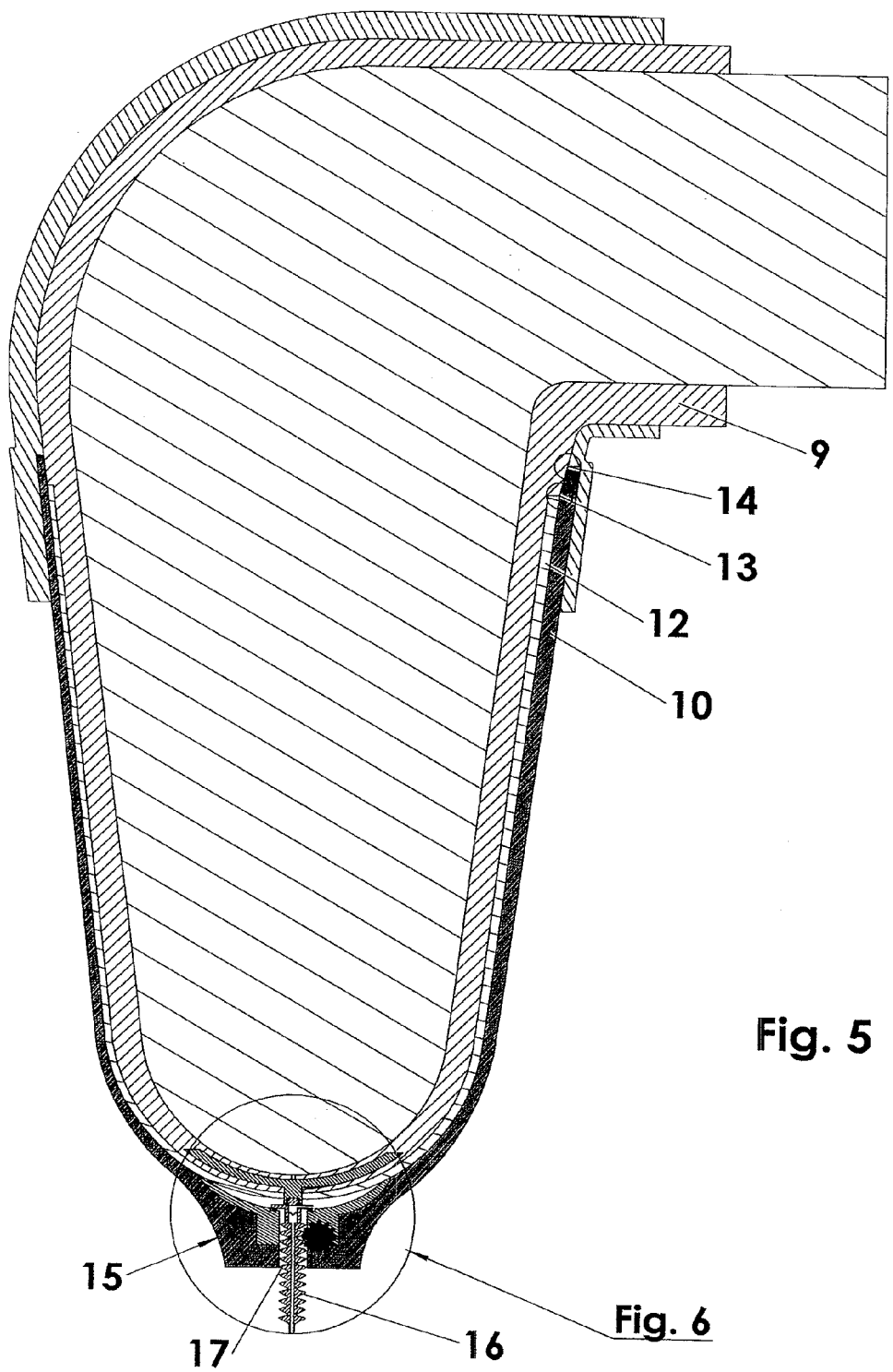
FIG. 5 is a cross-sectional view of the prosthetic assembly of the present invention similar to FIG. 4 including a locking pin (16) connected to the distal end of the liner (9) and cooperating with a locking assembly mounted in the distal end (15) of the socket (10).
FIG. 6 is an exploded view of the distal end of the prosthetic assembly of FIG. 5 illustrating the details of the locking pin (16) cooperating with the locking assembly mounted in the distal end of the socket and also the internal passageway through the pin having the one-way valve (19) therein permitting the exit of air from the volume of the interstitial region (12) to the surrounding atmosphere.
Figure 6:
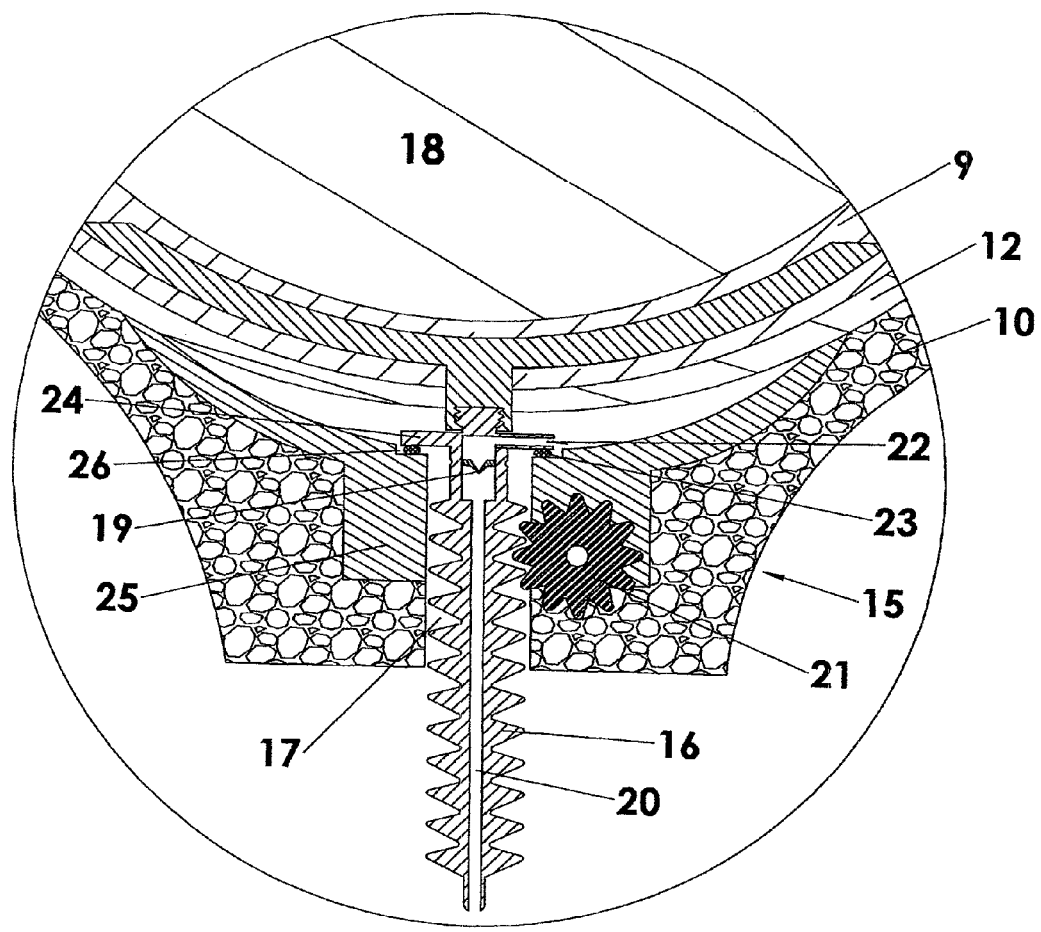

FIG. 5 is an illustration of another embodiment of the present invention similar to FIG. 4 including a locking assembly (15) mounted in the distal end of the socket (10) comprising a locking pin (16) which engages a hole or cavity (17) in the prosthetic socket for locking the prosthetic assembly onto the residual limb and which includes another air exit flow path for evacuating air within the interstitial region occupied by the compressible material.

FIG. 6 is an exploded view of the locking assembly in the distal end of the socket illustrated in FIG. 5. A pin receiving housing (25) is mounted within the distal end of socket (10) and includes a hole or cavity (17) therethrough for receiving locking pin (16). The locking pin (16) has an upper radially extending flange (24) with one or more laterally extending passageways (22). The locking pin further includes an axially extending passageway (20) fluidically communicating with the one or more lateral passageways (22) which, it turn, are in fluidic communication with the interstitial volume occupied by material or fabric layer (12) bound by liner (9) and socket (10). The passageway (20) includes a one-way valve (19) therein which may be any typical type of one-way valve such as a duck-bill valve or spring biased ball check valve. An O-ring (23) is disposed in an annular recess (26) to provide a sealing engagement between the pin flange (24) and the pin receiving housing (25). Although FIG. 6 shows a single O-ring (23), it is contemplated that any type of sealing means could be employed as along as the air passage is restricted to flow from the interstitial volume through the one-way valve (19) and out through the passageway (20). The locking assembly (15) further includes a locking ratchet wheel (21) for engaging annular recesses on the locking pin (16) for locking the pin within hole (17). It is noted that the locking assembly is not limited to that shown in the drawings wherein pin (16) could have a different exterior configuration that would cooperate with any other type of locking mechanism as, for example, the locking assembly disclosed in U.S. Pat. No. 7,427,298 which is incorporated herein by reference in its entirety.

Furthermore, although not shown in FIG. 6, the distal end of the socket (10) may be configured to be connected to a pylon of a prosthetic leg (not shown) via any commercially available mechanism such as the one disclosed in U.S. Pat. No. 3,659,294 which is incorporated herein by reference.

The foregoing relates to the preferred exemplary embodiments of the invention, it being understood that other variants and embodiments thereof are possible within the spirit and scope of the invention, the latter being defined by the appended claims.

What is claimed is:

1. A prosthetic assembly comprising:
   a) a monolithic prosthetic socket having an inner surface and an outer surface, a closed distal end and an open proximal end; said inner surface configured to substantially be complimentary to the shape of a residual limb of an amputee; said socket having a proximal end edge and a proximal outer surface region surrounding said open proximal end;
   b) a prosthetic liner having an inner surface and an outer surface, a closed distal end and an open proximal end; said inner surface adapted to conform to the shape of the residual limb of the amputee such that said limb is fittingly retained therein when donned; said liner having a proximal outer surface region surrounding said proximal open end extending from a proximal end edge of said liner to an intermediate edge thereon; said liner having a distal outer surface region extending from said intermediate edge to said distal end and being covered with a porous or continuously cavitated compressible material having an outer surface; said proximal outer surface region of said liner and said outer surface of said compressible material defining a substantially collinear outer surface with the compressible material layer being recessed into said liner to a distance of about the thickness of the compressible material;
   c) said liner being mounted within said socket such that said outer surface of said compressible material is fittingly received in said socket and in direct contact with the inner surface of said monolithic socket from said intermediate edge to said distal end of said liner to thereby define and sustain an interstitial area between the inner surface of said socket and the outer surface of said liner through said compressible material;
   d) said liner, when mounted in said socket, having said intermediate edge disposed proximate said proximal edge of said socket and within said socket such that said proximal outer surface region of said liner is in direct contact with the inner surface of said monolithic socket from said intermediate edge of said liner to said proximal end edge of said socket and extends away from said proximal end edge of said socket;
   e) a sealing open-ended sleeve having a first end and an opposite second end; said sealing sleeve mounted in sealing engagement over said proximal outer surface region of said socket and said proximal outer surface region of said liner with said first end overlapping said proximal outer surface region of said socket and said second end overlapping and terminating within said proximal outer surface region of said liner; whereby as said amputee ambulates, air trapped within said interstitial area is forced to evacuate therefrom through said compressible material, through the interface between said proximal outer surface region of said liner and the inner surface of said monolithic socket from said intermediate edge of said liner to said proximal end edge of said socket and through the interface between said sealing sleeve, said proximal outer surface region of said socket and said proximal outer surface region of said liner;
   f) said liner, said compressible material and said sealing sleeve comprising materials selected such that a vacuum from above about 0 inches Hg to about 15 inches Hg is capable of being maintained in said interstitial area upon ambulatory motion; and
   g) said socket includes a distally located hole or cavity extending therethrough and said liner comprises a locking pin in the distal end which engages said hole or cavity in the distal end of said socket for locking the prosthesis onto the residual limb of the amputee, said pin further includes an axially extending passageway with a one-way valve mounted therein for permitting exit of air in the volume of said interstitial area during ambulation of the amputee;
   h) whereby a circumferentially continuous sealable interface between said liner and said socket together with a circumferentially continuous sealable interface between said sleeve and said liner provides sufficient sealing structure free of any concentrated annular pressure points to accomplish said vacuum within said prosthetic assembly.

2. A prosthetic assembly as claimed in claim 1, wherein said liner is made from an elastomer and said compressible material is a fabric or foam.

3. A prosthetic assembly as claimed in claim 2, wherein said elastomer comprises one or more of the polymer materials from the list consisting of the following types: polyurethane, polybutylene, polypropylene, and styrene block copolymers.

4. A prosthetic assembly as claimed in claim 2, wherein said fabric or foam is bonded to said liner.

5. A prosthetic assembly as claimed in claim 1, wherein said liner is made from an elastomer and said compressible material is formed by treating the outer surface of the elastomer to cause the outer surface to form a foam.

6. A prosthetic assembly as claimed in claim 1, wherein said liner, said compressible material and said sealing sleeve comprising materials selected such that said vacuum is from about 2 inches Hg to about 14 inches Hg and is capable of being maintained in said interstitial area upon ambulatory motion.

7. A prosthetic assembly as claimed in claim 1, wherein said liner, said compressible material and said sealing sleeve comprising materials selected such that said vacuum is from about 5 inches Hg to about 12 inches Hg and is capable of being maintained in said interstitial area upon ambulatory motion.

8. A prosthetic assembly as claimed in claims 1, further including an adhesive, disposed on said proximal outer surface region of said socket and said proximal outer surface region of said liner, and which is mild and temporary such that it improves the vacuum-holding power of the seal between said sealing sleeve, socket and liner yet allows the sleeve to be removed, undamaged by the wearer.

9. A prosthetic assembly as claimed in claim 1, wherein a length of the elastomeric liner from said open proximal end to closed distal end is in the range of from 9 to 24 inches; and wherein said compressible material on the outer surface of said liner extends from the closed distal end for a distance in the range of from about 4 to 21 inches toward the open proximal end thereby not reaching said open proximal end.

10. A prosthetic assembly as claimed in claim 1, wherein a length of the elastomeric liner from said open proximal end to closed distal end is in the range of from 8 to 20 inches; and wherein said compressible material on the outer surface of said liner extends from the closed distal end for a distance in the range of from about 4 to 16 inches toward the open proximal end thereby not reaching said open proximal end.

11. A prosthetic assembly as claimed in claim 1, wherein said locking pin further comprises a first end connected to said distal end of said liner and defining a flange with at least one laterally extending passageway in fluidic communication with said axially extending passageway.

12. A prosthetic assembly as claimed in claim 11, wherein said flange is in sealing engagement with a pin receiving housing whereby air flow from said interstitial region is restricted to flow from said interstitial region through said at least one lateral passageway, through said one-way valve and out through said axially extending passageway.

13. A prosthetic assembly as claimed in claim 12, wherein said sealing engagement comprises an O-ring.

14. A prosthetic assembly as claimed in claim 1, wherein said socket distal end has a pin receiving housing mounted therein and defining said hole or cavity for receiving said locking pin.

15. A prosthetic assembly as claimed in claim 14, wherein said pin and said pin receiving housing further comprise a locking mechanism for locking said pin in said hole or cavity.

16. A prosthetic assembly as claimed in claim 15, wherein said locking mechanism comprises a ratchet wheel.

* * * * *